US008877962B2

(12) United States Patent
Nakano et al.

(10) Patent No.: US 8,877,962 B2
(45) Date of Patent: Nov. 4, 2014

(54) MANUFACTURING METHOD FOR SULFONIC ACID GROUP-CONTAINING ETHER COMPOUND

(71) Applicant: Nippon Shokubai Co, Ltd, Osaka (JP)

(72) Inventors: Masato Nakano, Suita (JP); Akihiko Kanzaki, Suita (JP); Takahiro Tsumori, Suita (JP)

(73) Assignee: Nippon Shokubai Co, Ltd, Osaka (JP)

( * ) Notice: Subject to any disclaimer, the term of this patent is extended or adjusted under 35 U.S.C. 154(b) by 0 days.

(21) Appl. No.: 14/304,382

(22) Filed: Jun. 13, 2014

(65) Prior Publication Data

US 2014/0296565 A1 Oct. 2, 2014

Related U.S. Application Data

(62) Division of application No. 13/063,563, filed as application No. PCT/JP2009/066008 on Sep. 14, 2009, now Pat. No. 8,779,184.

(30) Foreign Application Priority Data

Sep. 12, 2008 (JP) .................................. 2008-234243

(51) Int. Cl.
C07C 309/00 (2006.01)
C07C 309/20 (2006.01)

(52) U.S. Cl.
CPC .................................. C07C 309/20 (2013.01)
USPC ...................................................... 562/110

(58) Field of Classification Search
CPC .............................. C07C 303/02; C07C 303/32
USPC ...................................................... 562/110
See application file for complete search history.

(56) References Cited

U.S. PATENT DOCUMENTS

| 4,029,583 | A | 6/1977 | Ho Chang et al. |
| 4,387,069 | A | 6/1983 | Murase |
| 5,376,148 | A | 12/1994 | Schafflutzel |
| 6,126,859 | A | 10/2000 | Hunter et al. |
| 2002/0016430 | A1* | 2/2002 | Yamaguchi et al. .......... 526/277 |

FOREIGN PATENT DOCUMENTS

| EP | 0564248 A1 | 10/1993 |
| EP | 1158009 A2 | 11/2001 |
| JP | 11-302341 | 11/1999 |
| JP | 2005-264190 | 9/2005 |

OTHER PUBLICATIONS

Tang et al., "Studies on the Preparation of Stable and High Solid Content Emulsifier-Free Latexes and Characterization of the Obtained Copolymers for MMA/BA System with the Addition of AHPS," Journal of Applied Polymer Science, vol. 79, 21-28 (2001).
Sosnovskii et al., "Alkoxylation of Substituted Oxiranes by Alkoxytitanium Tosylates", Russian Journal of Organic Chemistry, vol. 29, No. 1.1, 1993, pp. 63-66 (XP008158322).
Daniel Swern, "Reactions of the Oxirane Group", Journal of the American Oil Chemists' Society, vol. 47, Nov. 1970, pp. 424-429.

* cited by examiner

*Primary Examiner* — Fereydoun G Sajjadi
*Assistant Examiner* — Kofi Adzamli
(74) *Attorney, Agent, or Firm* — Novak Druce Connolly Bove + Quigg LLP

(57) ABSTRACT

The present invention provides a method for efficiently producing a sulfonic acid group-containing ether compound having a high purity and a good polymerizability while preventing production of a byproduct, and provides a sulfonic acid group-containing ether compound containing fewer impurities and having a good radical (co)polymerizability.

The present invention provides a method of producing a sulfonic acid group-containing ether compound by reacting a sulfurous acid compound with a compound represented by the formula (1):

[Chem. 1] (1)

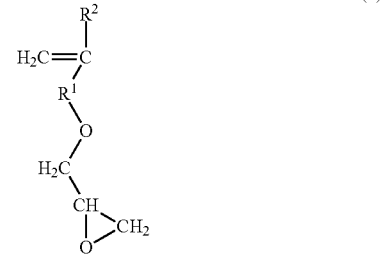

wherein $R^1$ represents a single bond, a $CH_2$ group, or a $CH_2CH_2$ group, and $R^2$ represents H, or a $CH_3$ group, the method comprising the steps of:

adjusting pH of a reaction system to 5.5 or greater with use of an alkaline substance; and adding the compound represented by the formula (1) to a reaction vessel containing the sulfurous acid compound.

1 Claim, No Drawings

US 8,877,962 B2

MANUFACTURING METHOD FOR SULFONIC ACID GROUP-CONTAINING ETHER COMPOUND

CROSS REFERENCE TO RELATED APPLICATIONS

This application is a Divisional of co-pending U.S. application Ser. No. 13/063,563 filed on Mar. 11, 2011, which is a National Phase filing under 35 U.S.C. §371 of PCT/JP2009/066008 filed on Sep. 14, 2009; and this application claims priority to Application No. 2008-234243 filed in Japan on Sep. 12, 2008 under 35 U.S.C. §119; the entire contents of all are hereby incorporated by reference.

TECHNICAL FIELD

The present invention relates to a method of producing a sulfonic acid group-containing ether compound. More specifically, the present invention relates to a method of producing a sulfonic acid group-containing ether compound comprising an unsaturated double bond, a sulfonic acid (salt) group, and an ether bond.

BACKGROUND ART

A typical sulfonic acid group-containing ether compound comprising an unsaturated double bond, a sulfonic acid (salt) group, and an ether bond is 3-allyloxy-2-hydroxy-1-propanesulfonic acid sodium salt (hereinafter, also referred to as "HAPS"). A known method of producing HAPS comprises the steps of: reacting 1 mol of allyl alcohol with 1 mol of epichlorohydrin at 100° C. for four hours; adding 1 mol of sodium sulfite dissolved in water thereto; and reacting the mixture at 90° C. for five hours (Non-Patent Document 1). Each of Patent Documents 1 and 2 discloses that HAPS is obtainable by reacting allyl glycidyl ether with sodium bisulfite added thereto. Additionally, a polymer comprising sodium acrylate and a sulfonic acid group-containing ether compound such as HAPS is known to be favorably used in a scale inhibitor, a corrosion inhibitor, and the like (see Patent Document 3, for example).

PRIOR ART DOCUMENT

Patent Document

Patent Document 1: JP 2002-138115 A (see [0080])
Patent Document 2: JP H-11-302341 A (see [0023])
Patent Document 3: JP 2005-264190

Non-Patent Document

Non-Patent Document 1: Journal of Applied Polymer Science Vol. 79, pp 21-28 (2001)

SUMMARY OF THE INVENTION

Problems to be Solved by the Invention

As above mentioned, each of Non-Patent Document 1, and Patent Documents 1 and 2 discloses a method of producing HAPS, and Patent Document 3 discloses an application of the polymer using HAPS. However, in the conventional method, the yield rate of HAPS is poor and a lot of byproducts such as 3-allyloxy-1,2-dihydroxypropane are produced, resulting in problems that the polymerizability of HAPS is lowered and the performance of the obtained polymer is insufficient when HAPS is used as a polymer material. The sulfonic acid group-containing ether compound having a lot of impurities hardly has fine polymerizability. Therefore, in order to produce a (co)polymer comprising a sulfonic acid group-containing ether compound as a raw material, it has been needed to select a technique such as polymerization under severe conditions to reduce residual monomers, use of a large amount of a polymerization initiator, and limitation on the monomer composition ratio. Accordingly, there has been still a room for improvement in facilitation of production of a sulfonic acid group-containing ether compound having a high purity and a good polymerizability. In addition, there has been still a room for production of a sulfonic acid group-containing ether compound having a higher purity and a better polymerizability.

Considering the above-described state of the art, the present invention has been devised. The object of the present invention is to provide a method for efficiently producing a sulfonic acid group-containing ether compound having a high purity and a good polymerizability while preventing production of a byproduct, and to provide a sulfonic acid group-containing ether compound containing fewer impurities and having a good radical (co)polymerizability.

Means for Solving the Problems

The present inventors have examined various methods of producing a sulfonic acid group-containing ether compound such as 3-allyloxy-2-hydroxy-1-propanesulfonic acid sodium salt (HAPS). Then, the present inventors have found out that a specific reaction mode inhibits a secondary reaction and allows a high-yield and easy production of a sulfonic acid group-containing ether compound having a high purity and fewer byproducts. The specific reaction mode refers to a mode in which a reaction between a sulfurous acid compound as a raw material and a specific ether compound (compound represented by formula (1)) such as allyl glycidyl ether is carried out by adding the specific ether compound to the sulfurous acid compound. In addition, the present inventors have found out that pH adjustment of a reaction system increases that effect. Thereby, the present inventors solved the above problems. Further, a composition containing the sulfonic acid group-containing ether compound obtainable by the method has few impurities and highly-pure sulfonic acid group-containing compound. Therefore, the composition has an excellent polymerizability so as to produce a polymer excellent in scale inhibition ability and cleaning capability when used as a polymer material. The polymer is suitably used in chemicals for water treatment, detergent builders, detergent compositions, dispersants, detergents and the like. Thereby, the present invention has been completed.

In the present invention, reaction carried out by adding a specific ether compound to a sulfurous acid compound is a necessary step. This allows high-yield and easy production of a sulfonic acid group-containing ether compound having a high purity and fewer byproducts. Accordingly, the present inventors found out that the effect is exerted because of a specific addition manner of raw materials. Also in this regard, the present invention has an important technical meaning.

The present invention provides a method of producing a sulfonic acid group-containing ether compound by reacting a sulfurous acid compound with a compound represented by the formula (1):

[Chem. 1]

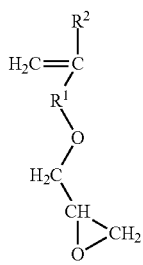
(1)

wherein $R^1$ represents a single bond, a $CH_2$ group, or a $CH_2CH_2$ group, and $R^2$ represents H, or a $CH_3$ group, the method comprising the steps of:

adjusting pH of a reaction system to 5.5 or greater with use of an alkaline substance; and adding the compound represented by the formula (1) to a reaction vessel containing the sulfurous acid compound.

The present invention also provides a composition comprising sulfonic acid group-containing ether compound represented by the formula (2), wherein the composition has pH of 10 or greater, and the composition comprises, with respect to 100 mol % of the compound represented by the formula (2), less than 10 mol % of a compound represented by the formula (3):

[Chem. 2]

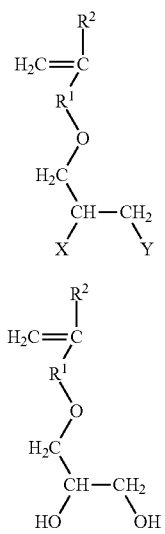

(2)

(3)

wherein $R^1$ represents a single bond, a $CH_2$ group, or a $CH_2CH_2$ group, $R^2$ represents H, or a $CH_3$ group, X and Y may be the same as or different from each other and each represent a hydroxy group or a sulfonic acid (salt) group, and at least one of X and Y is a sulfonic acid (salt) group.

Hereinafter, the present invention is described in detail.

<Method of Producing a Sulfonic Acid Group-Containing Ether Compound>

The method of producing a sulfonic acid group-containing ether compound of the present invention is a method for reacting the compound represented by the formula (1) with a sulfurous acid compound. Here, it is to be noted that the reaction between the compound represented by the formula (1) and a sulfurous acid compound is also simply referred to as "reaction".

In the compound represented by the formula (1), $R^1$ represents a single bond, a $CH_2$ group, or a $CH_2CH_2$ group. Among these, $R^1$ preferably represents a $CH_2$ group. Namely, the compound represented by the formula (1) is preferably a compound represented by the formula (1) in which $R^1$ is a $CH_2$ group. In the case where $R^1$ is a $CH_2$ group, the scale inhibition ability is further improved in the polymer obtained by polymerizing a sulfonic acid group-containing ether compound that is obtainable by using the above compound as a raw material. From the standpoint of further improving the scale inhibition ability of the polymer, (meth)allylglycidyl ether is particularly preferable as the compound represented by the formula (1).

Preferable examples of the sulfurous acid compound include sulfurous acid, hydrogen sulfite, dithionous acid, metabisulfurous acid, and salts of these. The sulfurous acid compound may be used in a form of acid (i.e. sulfurous acid and the like). However, from the standpoint of handling ease and improvement in the yield rate, it is preferably added in a form of salt. Namely, the sulfurous acid compound is preferably salt. Further, the sulfurous acid compound more preferably comprises at least one kind of salt selected from the group consisting of sulfite salts, bisulfite salts, dithionite salts, and metabisulfite salts. In particular, the sulfurous acid compound preferably comprises a lower oxide, such as sodium bisulfite, potassium bisulfite, sodium dithionite, potassium dithionite, sodium metabisulfite, and potassium metabisulfite, or a salt thereof. From the standpoint of the cost efficiency and improvement in the yield rate, the sulfurous acid compound more preferably comprises bisulfite salts and metabisulfite salts, and particularly preferably comprises sodium bisulfite and sodium metabisulfite.

Examples of the salts include metal salts, ammonium salts, and organic amine salts. More specifically, examples of the salts include: alkali metal salts such as sodium salt and potassium salt; alkaline earth metal salts such as magnesium salt, calcium salt, strontium salt, and barium salt; salts such as aluminum salt and iron salt; ammonium salt; alkanolamine salts such as monoethanolamine salt, diethanolamine salt, and triethanolamine salt; alkylamine salts such as monoethylamine salt, diethylamine salt, and triethylamine salt; and polyamine salts such as ethylenediamine salt and triethylenediamine salt.

The method comprises the steps of: adjusting pH of a reaction system to 5.5 or greater with use of an alkaline substance (hereinafter, also referred to as "pH adjustment step"); and adding the compound represented by the formula (1) to a reaction vessel containing the sulfurous acid compound (hereinafter, also referred to as "addition step"). Here, the method may further comprise another step that may be carried out in a common method, as long as it does not adversely affect the effect of the present invention.

In the pH adjustment step, pH of a reaction system is adjusted to 5.5 or greater with use of an alkaline substance. At that time, the reaction system (which refers to the inside of the reaction vessel, more preferably, a solution in the reaction vessel) preferably comprises an aqueous solution of a sulfurous acid compound and an alkaline substance. Namely, it is preferable to adjust pH of the reaction system by mixing the alkaline substance and the aqueous solution of a sulfurous acid compound. For example, such adjustment of pH to 5.5 or greater is carried out by (1) adding an aqueous solution of a sulfurous acid compound to a reaction vessel containing an alkaline substance and mixing them, (2) adding an alkaline substance to a reaction vessel containing an aqueous solution of a sulfurous acid compound, or (3) simultaneously adding an aqueous solution of a sulfurous acid compound and an alkaline substance to a reaction vessel and mixing them. Any of the above methods can be employed. In particular, from the standpoint of inhibiting generation of sulfurous acid gas, the adjustment (1) (pH is adjusted to 5.5 or greater by adding an aqueous solution of a sulfurous acid compound to a reaction vessel containing an alkaline substance and mixing them) is most preferable. In the adjustment (1), only a part of entire the alkaline substance needed to adjust pH to 5.5 or greater may be added prior to the addition of the aqueous solution of a sulfurous acid compound and the rest of the alkaline substance may be added together with the aqueous solution of a sulfurous acid compound. However, the entire alkaline substance is preferably added to the reaction vessel first.

The pH value of the reaction system adjusted in the pH adjustment step is preferably 5.5 or greater. The pH value of less than 5.5 may lower the yield rate of the obtainable sulfonic acid group-containing ether compound. The reason for this is not sufficiently clear yet. In the present invention, when a compound represented by the formula (1) is added to the reaction vessel containing a sulfurous acid compound, the low pH may cause discharge of the sulfurous acid gas outside the system. This presumably leads to the lowered yield rate of the obtainable sulfonic acid group-containing ether compound. The pH value of 5.5 or greater leads to the effect of inhibiting generation of sulfurous acid gas. The pH value is more preferably 5.7 or greater, further preferably 6.0 or greater, and particularly preferably 6.1 or greater. The upper limit of the pH value is not particularly limited, and is preferably pH 14 or lower.

The alkaline substance usable in the above adjustment is not particularly limited, and examples thereof include hydroxides of alkaline metals such as sodium hydroxide and potassium hydroxide, hydroxides of alkaline earth metals such as calcium hydroxide, ammonia, and amines. Each of these may be used alone or two or more of these may be used in combination.

The amount of the alkaline substance is not particularly limited as long as it is an enough amount to adjust the pH of the reaction system to 5.5 or greater. For example, the amount is preferably 0.1 mol or more, more preferably 0.2 mol or more, and further preferably 0.3 mol or more, with respect to 1 mol of the compound represented by the formula (1). The amount is preferably 1 mol or less, more preferably 0.8 mol or less, and further preferably 0.36 mol or less.

In the addition step, a compound represented by the formula (1) is added to a reaction vessel containing a sulfurous acid compound. Here, the time point when both a compound represented by the formula (1) and a sulfurous acid compound are added to a reaction vessel is referred to as "at the start of the reaction between a compound represented by the formula (1) and a sulfurous acid compound (also simply referred to as "at the start of the reaction")". The time point before the start of the reaction is referred to as "before the start of the reaction". Accordingly, in the case where the addition is carried out after the pH adjustment, the pH adjustment is carried out "before the start of the reaction".

In addition, "the reaction vessel" is a reaction vessel for carrying out a reaction between a compound represented by the formula (1) and a sulfurous acid compound, and may be a tank-type or tube-type vessel. Further, "addition to a reaction vessel containing a sulfurous acid compound" refers to a state where a sulfurous acid compound is present in the reaction vessel when a compound represented by the formula (1) is added to the vessel.

A part or the entire amount of the sulfurous acid compound is preferably added to the reaction vessel before the start of the reaction (initial placement). For example, when the entire amount is 100 mol %, the amount of the initial placement is preferably 50 mol % or more, more preferably 80 mol % or more, and further preferably 100 mol % (namely, the entire amount). Instead of the initial placement, it is also preferable to add 80 mol % or more, more preferably 100 mol % of the sulfurous acid compound in the entire amount of 100 mol % thereof to the vessel at a very early stage of the reaction (at a very early stage after the start of the reaction), for example, prior to the addition of 50 mol % or more of the compound represented by the formula (1) in the entire amount of 100 mol % thereof.

The amount of the sulfurous acid compound is preferably 0.9 mol or more and 1.3 mol or less in the stoichiometric amount, with respect to 1 mol of the compound represented by the formula (1). What is meant by "in the stoichiometric amount" is described in the following. For example, in this case, an amount of 1 mol of sodium bisulfite used as a sulfurous acid compound reacts with 1 mol of the compound represented by the formula (1), and therefore, the amount of sodium bisulfite is preferably 0.9 mol or more and 1.3 mol or less. In contrast, an amount of ½ mol of sodium metabisulfite used as a sulfurous acid compound reacts with 1 mol of the compound represented by the formula (1), and therefore, the amount of sodium metabisulfite is preferably 0.45 mol or more and 0.65 mol or less, which is the ½ molar amount. When the amount is less than 0.9 mol in the stoichiometric amount, there may be a case where the compound represented by the formula (1) remaining unreacted increases or a lot of byproducts are produced. Further, when the amount is more than 1.3 mol in the stoichiometric amount, the byproducts derived from the sulfurous acid compound may increases. The amount of the sulfurous acid compound is more preferably 0.95 mol or more, further preferably 0.97 mol or more in the stoichiometric amount, with respect to 1 mol of the compound represented by the formula (1). Additionally, the amount of the sulfurous acid compound is more preferably 1.2 mol or less, and further preferably 1.1 mol or less.

In the addition step, the compound represented by the formula (1) is added to the reaction vessel containing the sulfurous acid compound. This inhibits a secondary reaction so as to improve the yield rate of the sulfonic acid group-containing ether compound.

A part of the compound represented by the formula (1), out of the total amount thereof, may be initially placed in the reaction vessel. However, from the standpoint of improving the yield rate of the sulfonic acid group-containing ether compound, 60 mol % or more, out of 100 mol % in total, of the compound represented by the formula (1) is preferably added to the reaction vessel at the start of the reaction or later. More preferably 80 mol % or more, and further preferably 100 mol %, namely, the total amount of the compound is preferably added to the reaction vessel at the start of the reaction or later. Here, "at the start of the reaction or later" refers to the time point when the reaction starts or the time point after the start of the reaction.

In the addition step, the compound represented by the formula (1) may be added continuously or dividedly. Further, the compound represented by the formula (1) may be added as it stands or after being diluted with a solvent in which the compound can be dissolved or dispersed. In the case of using a solvent, it is preferable to use a solvent which is inert to a glycidyl group contained in the compound represented by the formula (1). The solvent may be appropriately selected in consideration of the ability to dissolve the compound represented by the formula (1). Here, it is preferable not to use a solvent, from the standpoint of using the composition containing the obtained sulfonic acid group-containing ether compound (composition commonly containing a reaction solvent and byproducts, in addition to the sulfonic acid group-containing ether compound) for various applications without additional treatment.

A particularly preferable mode of the addition step is a mode in which the compound represented by the formula (1) is dropped to the reaction vessel containing the sulfurous acid compound. The addition rate (preferably, the dropping rate) is preferably set to 0.01 to 10% by mass, out of the 100% by mass in total, of the compound represented by the formula (1) per minute. The addition rate within this range allows an efficient and sufficient reaction between the compound represented by the formula (1) and the sulfurous acid compound. The addition rate (preferably, the dropping rate) is more preferably set to 0.5 to 5% by mass, out of the 100% by mass in total, of the compound represented by the formula (1) per minute. In addition, the addition rate (preferably, the dropping rate) may be constant or may be changed during the addition.

In the method, the addition step may be carried out after the pH adjustment step, or alternatively, the pH adjustment step and the addition step may be carried out simultaneously. However, it is preferable to carry out the addition step after the pH adjustment step.

Preferable modes of the method include the following modes A and B. In particular, the mode A is preferable.

Mode A: A part or the entire amount of an alkaline substance and the sulfurous acid compound, out of the total amount thereof, are initially placed in the reaction vessel. After the reaction system (which refers to the inside of the reaction vessel, more preferably the solution in the reaction vessel) is adjusted to have pH of 5.5 or greater, the compound represented by the formula (1) is added to the reaction vessel.

Mode B: A part or the entire amount of the sulfurous acid compound is initially placed in the reaction vessel. While the compound represented by the formula (1) is added to the reaction vessel, the reaction system is adjusted to have pH of 5.5 or greater.

In the case of the mode B, it is preferable to adjust the pH of the reaction system to 5.5 or greater as quickly as possible after the start of addition of the compound represented by the formula (1). When the reaction time at the pH of 5.5 or greater becomes longer in the entire reaction time, generation of sulfurous acid gas and production of byproducts are more efficiently reduced. For example, the reaction time at a pH of 5.5 or greater is preferably 90% or more, more preferably 95% or more, and further preferably 100%, that is, the entire reaction time, in the entire reaction time.

In the method, the reaction between the compound represented by the formula (1) and the sulfurous acid compound may be carried out under the air atmosphere. However, the reaction under the inert atmosphere such as nitrogen atmosphere is preferable because coloring can be avoided. In addition, the reaction is commonly carried out in a solvent. Though the solvent is not particularly limited, a solvent at least containing water (sole solvent of water or mixed solvent containing water and an organic solvent) is preferable. The water in the entire solvent is preferably 50% by mass or more, more preferably, 70% by mass or more, and most preferably 100% by mass. Namely, a sole solvent of water is most preferable. In addition, the solids concentration at the time of reaction (solids concentration when the reaction is completed) is preferably 20% by mass or more and 80% by mass or less.

The reaction is preferably carried out at a reaction temperature of 30° C. or higher and lower than 80° C. The reaction temperature lower than 80° C. can reduce production of byproducts, and the reaction temperature of 30° C. or higher is likely to improve the yield rate of the sulfonic acid group-containing ether compound as a target object. The reaction temperature is more preferably 50° C. or higher and lower than 75° C., and further preferably 58° C. or higher and lower than 68° C.

The most preferable mode is that the entire reaction step in the method of the present invention is carried out at a reaction temperature within the above range. However, a mode is regarded to be preferable, in which the reaction is carried out at a reaction temperature within the above range for 30% or more of the entire reaction time. Moreover, a mode is regarded to be more preferable, in which the reaction is carried out at a reaction temperature within the above range for 50% or more of the entire reaction time.

In the method, after the addition step (step of adding the compound represented by the formula (1)), a reaction may be further continued (such reaction may also be referred to as "post-reaction step"). This further improves the yield rate of the sulfonic acid group-containing ether compound.

Addition of the compound represented by the formula (1) (namely, start of the addition step) starts the reaction between the sulfurous acid compound and the compound represented by the formula (1), and therefore, "the entire reaction step" in the present description include the addition step and the post-reaction step.

The sulfonic acid group-containing ether compound obtained in the method is represented by the following formula (2):

[Chem. 3]

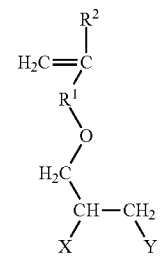

(2)

wherein R1 represents a single bond, a $CH_2$ group, or a $CH_2CH_2$ group, $R^2$ represents H, or a $CH_3$ group, X and Y may be the same as or different from each other and each represent a hydroxy group or a sulfonic acid (salt) group, and at least one of X and Y is a sulfonic acid (salt) group.

In the formula (2), X and Y are groups derived from the sulfurous acid compound and at least one of the two is a sulfonic acid (salt) group. In particular, it is preferable that one of X and Y is a sulfonic acid (salt) group and the other is a hydroxy group.

Here, the sulfonic acid (salt) group is a group represented by —$SO_3Z$ (Z is a hydrogen atom, metal atom, ammonium group, or organic amine group). Preferable examples of the metal atom include alkali metals such as sodium and potassium; alkali earth metals such as magnesium, calcium, strontium, and barium; aluminum and iron. Preferable examples of the organic amine group include alkanolamine groups such as a monoethanolamine group, a diethanolamine group, and a triethanolamine group; alkylamine groups such as a monoethylamine group, a diethylamine group, and a triethylamine group; and polyamine groups such as an ethylenediamine group and a triethylenediamine group. More preferable examples of the sulfonic acid (salt) group include a sulfonic acid group, a lithium sulfonate group, a potassium sulfonate group, a sodium sulfonate group, an ammonium sulfonate group, and a quaternary amine group of sulfonic acid.

In the formula (2), $R^1$ and $R^2$ are dependent on $R^1$ and $R^2$ in the compound represented by the formula (1) as a raw material. As above described, the compound represented by the formula (1) is preferably a compound in which $R^1$ represents a $CH_2$ group, and therefore, the compound represented by the formula (2) is also preferably a compound in which $R^1$ represents a $CH_2$ group. In the case where $R^1$ is a $CH_2$ group, the scale inhibition ability of the polymer obtained by polymerizing the sulfonic acid group-containing ether compound is further improved.

The sulfonic acid group-containing ether compound is more preferably 3-(meth)allyloxy-2-hydroxy-1-propane sodium sulfonate.

The method of the present invention enables efficient and easy production of a highly-pure sulfonic acid group-containing ether compound (compound represented by the formula (2)) comprising fewer impurities. The sulfonic acid group-containing ether compound obtained in this manner has fewer impurities and is highly pure, and therefore, it has fine radical (co)polymerizability. Accordingly, when the compound is used as a polymer material, a polymer excellent in scale inhibition ability can be obtained and is suitably used in chemicals for water treatment, detergent builders, detergent compositions, dispersants, cleaners, and the like. Accordingly, one of the preferable embodiments of the present invention include chemicals for water treatment, detergent builders, detergent compositions, dispersants, cleaners, and the like, which contain polymers obtained by polymerizing the monomer component comprising the sulfonic acid group-containing ether compound.

<Composition Containing the Sulfonic Acid Group-Containing Ether Compound>

The composition containing the sulfonic acid group-containing ether compound of the present invention comprises the sulfonic acid group-containing ether compound represented by the formula (2) and is obtainable by the above method of producing the sulfonic acid group-containing ether compound. Also from the standpoint of easy production, the composition is preferably produced by the above method of producing the sulfonic acid group-containing ether compound. Therefore, one of the preferable embodiments of the present invention is an embodiment in which the composition containing the sulfonic acid group-containing ether compound of the present invention is obtained by the above method. In this case, the composition containing the sulfonic acid group-containing ether compound necessarily comprises the sulfonic acid group-containing ether compound, and further comprise byproducts (for example, the compound represented by the formula (3)) and a reaction solvent such as water in some cases. In addition, the composition containing the sulfonic acid group-containing ether compound is preferably in the form of a solution, and more preferably in the form of an aqueous solution. The composition in the form of an aqueous solution may be prepared by using a solvent containing at least water as a reaction solvent in the above method of producing the sulfonic acid group-containing ether compound.

The compound represented by the formula (3) tends to be secondarily produced in a reaction between the compound represented by the formula (1) and the sulfurous acid compound. The amount of the compound represented by the formula (3) in the composition containing the sulfonic acid group-containing ether compound is preferably less than 10 mol % with respect to 100 mol % of the compound represented by the formula (2). In the present invention, employment of the above method of producing the sulfonic acid group-containing ether compound allows sufficient reduction of the amount of the compound represented by the formula (3) as a byproduct in the composition containing the sulfonic acid group-containing ether compound. This leads to the higher purity of the sulfonic acid group-containing ether compound. Accordingly, when such a composition containing sulfonic acid group-containing ether compound is used as a polymer material, it is possible to obtain a polymer particularly excellent in scale inhibition ability. From the standpoint of the performance of the polymer and the polymerizability of the sulfonic acid group-containing ether compound, the amount of the compound represented by the formula (3) is preferably less than 10 mol %, more preferably less than 5 mol %, and further preferably less than 3 mol %.

The amount of the compound represented by the formula (3) with respect to 100 mol % of the compound represented by the formula (2) is determined by liquid chromatography.

The composition containing the sulfonic acid group-containing ether compound is commonly obtained in the form of an alkaline solution (preferably, an alkaline aqueous solution) in the above method of producing the sulfonic acid group-containing ether compound. Accordingly, the composition containing the sulfonic acid group-containing ether compound preferably has pH of 10.0 or greater, more preferably 12.0 or greater, further preferably 12.5 or greater, and particularly preferably 13.0 or greater. In the case where the obtained composition containing the sulfonic acid group-containing ether compound has pH of 10.0 or greater, the composition containing the sulfonic acid group-containing ether compound has a smaller aging variation in the polymerizability even when stored in the form of the aqueous solution. Further, in accordance with the application, it is also possible to obtain a neutral or acid composition containing the sulfonic acid group-containing ether compound by neutralizing during or after the reaction. The upper limit of the pH value is not particularly limited and is preferably 14 or less.

In the case where the composition containing the sulfonic acid group-containing ether compound contains water, the amount of the water is preferably 40 parts or more and 99 parts or less with respect to 100 parts (by mass) of the composition.

Effect of the Invention

The method of producing the sulfonic acid group-containing ether compound of the present invention has the configuration as above described, and therefore, it is possible to easily produce a sulfonic acid group-containing ether compound having a high purity and fine polymerizability at a high yield rate. In addition, the composition containing the sulfonic acid group-containing ether compound of the present invention has fewer impurities and fine radical (co)polymerizability. Accordingly, when the compound is used as a polymer material, a polymer excellent in scale inhibition ability can be obtained. Such polymers may be suitably used in chemicals for water treatment, detergent builders, detergent compositions, dispersants, cleaners, and the like.

Mode for Carrying Out the Invention

Hereinafter, the present invention is described in more detail based on examples, but is not limited only to these examples. All parts are by mass unless otherwise specified, and percentages are by mass unless otherwise specified, except for the percentages for expressing the yield rate. The percentages for expressing the yield rate are simple percentages.

The quantity of the compound such as residual monomers was determined by high speed liquid chromatography. The determination was carried out under the following conditions.

<High Speed Liquid Chromatography>

The quantity was determined under the following conditions with use of "L-7100 type pump", "L-7300 type column oven", "L-7200 type auto sampler", and "L-7400 type UV detector" each manufactured by Hitachi, Ltd.

Column: "ShodexRSpak DE-413" manufactured by SHOWA DENKO K.K.
Eluant: 0.1% by weight phosphate solution
Flow rate: 1 ml/min.
Calibration curve: A reagent of 40% aqueous solution of 3-allyloxy-2-hydroxy-1-sodium propanesulfonate (manufactured by Aldrich chemical company Inc.) and 3-allyloxy-1,2-dihydroxypropane (manufactured by Wako Pure Chemical Industries, Ltd.) were used. The reagent of 40% aqueous solution of 3-allyloxy-2-hydroxy-1-sodium propanesulfonate had pH of 6.0. The present chromatography clarified that the reagent of 40% aqueous solution of 3-allyloxy-2-hydroxy-1-sodium propanesulfonate contains 11.9 mol % of 3-allyloxy-1,2-dihydroxypropane with respect to 100 mol % of 3-allyloxy-2-hydroxy-1-sodium propanesulfonate.
Temperature: 40° C.

EXAMPLE 1

Along with the introduction of nitrogen, 0.81 parts of deionized water and 0.37 parts of a 48% aqueous sodium hydroxide solution were put into a reaction vessel (made of SUS) having a thermometer, a stirrer, a nitrogen inlet tube and a nitrogen outlet provided with a cold trap. An amount of 2.60 parts of 35% aqueous acid sodium sulfite solution was added thereto. At the time, the pH of the reaction liquid was 6.6. The liquid was heated to 63° C. and 1.0 part of allyl glycidyl ether was dropped thereto over 120 minutes. At about 60 minutes after the start of dropping of the allyl glycidyl ether, pH was rapidly changed to strong alkaline. After completing the dropping of the allyl glycidyl ether, the reaction liquid was held to maintain the temperature at 63° C. for 30 minutes so that the reaction was completed (a product obtained in this manner is referred to as "composition (1) containing the sulfonic acid group-containing ether compound"). At the completion of the reaction, the pH was 13.9.

In the composition containing the sulfonic acid group-containing ether compound (1) as a product material, the yield rate of 3-allyloxy-2-hydroxy-1-sodium propanesulfonate (sulfonic acid group-containing ether compound of the present invention) was 94.9%. The percentage of 3-allyloxy-1,2-dihydroxypropane to 3-allyloxy-2-hydroxy-1-sodium propanesulfonate (namely, the amount of 3-allyloxy-1,2-dihydroxypropane with respect to 100 mol % of 3-allyloxy-2-hydroxy-1-sodium propanesulfonate) was 3.9 mol %.

COMPARATIVE EXAMPLE 1

Along with the introduction of nitrogen, 1 part of allyl glycidyl ether was put into a reaction vessel (made of SUS) having a thermometer, a stirrer, a nitrogen inlet tube, and a nitrogen outlet provided with a cold trap. An amount of 2.60 parts of 35% aqueous acid sodium sulfite solution and 1.18 parts of deionized water were added thereto. At the time, the pH of the reaction liquid was 4.8. After being heated to 90° C., the reaction liquid was reacted at 90° C. for five hours so that the reaction was completed. The yield rate of 3-allyloxy-2-hydroxy-1-propanesulfonic acid sodium salt (sulfonic acid group-containing ether compound) (allyl glycidyl ether base) was 84.5%. The amount of 3-allyloxy-1,2-dihydroxypropane with respect to 100 mol % of 3-allyloxy-2-hydroxy-1-propanesulfonic acid sodium salt was 14.9 mol %.

EXAMPLE 2

An amount of 328.5 parts of deionized water was put into a separable flask (made of SUS) provided with a reflux condenser and a stirrer. The deionized water was heated while being stirred, so as to be refluxed at the boiling point (hereinafter, such a state is referred to as "reflux at the boiling point"). In this manner, the deionized water was made into a polymerization reaction system. Next, the polymerization reaction system under stirring and under reflux at the boiling point was added with a mixed aqueous solution (433.6 parts in total) comprising 20.7 parts of a 80% aqueous acrylic acid solution (hereinafter, referred to as "80% AA") and 412.9 parts of 37% aqueous sodium acrylate solution (hereinafter, referred to as "37% SA"), 82.0 parts of a 40% aqueous 3-allyloxy-2-hydroxy-1-propanesulfonic acid sodium salt solution (hereinafter, referred to as "40% HAPS"), 28.7 parts (corresponding to 5 parts with respect to 1 mol of monomers in the monomer component) of a 35% aqueous hydrogen peroxide solution (hereinafter, referred to as "35% HP"), and 41.5 parts (corresponding to 3.1 parts with respect to 1 mol of monomers in the monomer component) of a 15% aqueous sodium persulfate solution (hereinafter, referred to as "15% NaPS"), and 96.6 parts of deionized water. The components were dropped from individual nozzles. In this manner, the reaction solution was prepared.

The drop time of the aqueous solutions and the deionized water was set to be 120 minutes for a mixed aqueous solution comprising 80% AA and 37% SA, 90 minutes for 40% HAPS, 120 minutes for 35% HP, and 140 minutes for 15% NaPS and for the deionized water. The dropping rate of each of the aqueous solutions and the deionized water was constant and the dropping of each of the aqueous solutions and the deionized water was carried out continuously.

After the dropping of the 15% NaPS and the deionized water, the reaction solution was further held (matured) under reflux at the boiling point for 60 minutes so that the polymerization reaction was completed. The amount of the remaining HAPS after the polymerization was measured to be 320 ppm.

Comparison between Example 1 and Comparative Example 1 clarified that the yield rate of the sulfonic acid group-containing ether compound was better in the method of the present invention than in a conventional method. In addition, Example 2 clarified that the sulfonic acid group-containing ether compound obtained in the method of the present invention has excellent polymerizability because it produces less residual sulfonic acid group-containing ether compound after the polymerization.

INDUSTRIAL APPLICABILITY

A composition containing the sulfonic acid group-containing ether compound of the present invention comprises a highly-pure sulfonic acid group-containing ether compound that exerts excellent polymerizability when the composition is used as a polymer material. In addition, when the sulfonic acid group-containing ether compound of the present invention is used as a polymerization material, the obtainable polymer shows high performance (in particular, scale inhibition ability and detergency) especially in aqueous applications so as to be suitably used in chemicals for water treatment, detergent builders, detergent compositions, dispersants, cleaners, and the like.

The invention claimed is:
1. A composition comprising sulfonic acid group-containing ether compound of formula (2),
wherein
the composition has pH of 10 or greater, and
the composition comprises, with respect to 100 mol % of the compound of formula (2), less than 10 mol % of a of formula (3):

[Chem. 2]

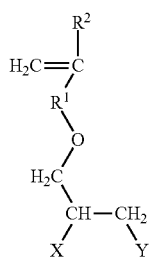

(2)

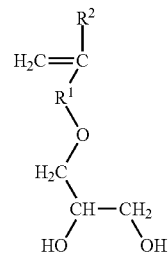

(3)

wherein $R^1$ represents a single bond, a $CH_2$ group, or a $CH_2CH_2$ group, $R^2$ represents H, or a $CH_3$ group, X and Y may be the same as or different from each other and each represent a hydroxy group or a sulfonic acid (salt) group, and at least one of X and Y is a sulfonic acid (salt) group.

* * * * *